United States Patent [19]

Bourland et al.

[11] 4,425,920
[45] Jan. 17, 1984

[54] APPARATUS AND METHOD FOR MEASUREMENT AND CONTROL OF BLOOD PRESSURE

[75] Inventors: Joe D. Bourland; Leslie A. Geddes; Charles F. Babbs; Willis A. Tacker, Jr., all of West Lafayette, Ind.

[73] Assignee: Purdue Research Foundation, West Lafayette, Ind.

[21] Appl. No.: 200,570

[22] Filed: Oct. 24, 1980

[51] Int. Cl.³ .............................................. A61B 5/02
[52] U.S. Cl. ................................... 128/672; 128/693; 128/691
[58] Field of Search ................................ 128/672–675, 128/214 E, 213 R, DIG. 12, 13, 640, 642, 679–680, 687–690, 691–693

[56] References Cited

U.S. PATENT DOCUMENTS

| | | | |
|---|---|---|---|
| 2,658,505 | 11/1953 | Sheer | 128/672 |
| 2,845,060 | 7/1958 | Roman | 128/672 |
| 3,095,872 | 7/1963 | Tolles | 128/672 |
| 3,132,643 | 5/1964 | Baum et al. | 128/672 |
| 3,592,187 | 7/1971 | Youdin et al. | 128/675 |
| 3,776,221 | 12/1973 | McIntyre | 128/672 |
| 3,871,361 | 3/1975 | Kamen | 128/672 |
| 4,080,966 | 3/1978 | McNally et al. | 128/214 E |

*Primary Examiner*—Kyle L. Howell
*Assistant Examiner*—Angela D. Sykes

*Attorney, Agent, or Firm*—O'Rourke & Harris

[57] ABSTRACT

Apparatus and method for measurement and control of blood pressure are disclosed. Blood pressure is indirectly continually monitored without use of a pressure transducer by sensing the pulse transit time to different sites in an artery, which transit time is inversely related to blood pressure, and developing pulses therefrom which are utilized to form arterial pulse waves, the comparison between which provide an indication of measured blood pressure. This indication is used to control blood pressure by controlling automatic release of a suitable drug into the body in amounts and over a time period as needed. The unit for measuring blood pressure includes two sets of electrodes positioned adjacent to but outside an artery at two sites (with the electrodes implanted or outside the body). Each electrode set is connected with an alternating current generator to supply alternating current at a low level to the electrodes and with demodulators to produce pulses due to a change of impedance offered to the supplied alternating current at each site. Each demodulator is connected with a detector to sense pulse arrival, and the detectors are connected with a time-interval measuring circuit. The system for control of blood pressure includes a blood pressure measuring unit that is connected with an electronic processing unit which controls a drug dispensing unit implanted in the body or attached outside the body.

3 Claims, 23 Drawing Figures

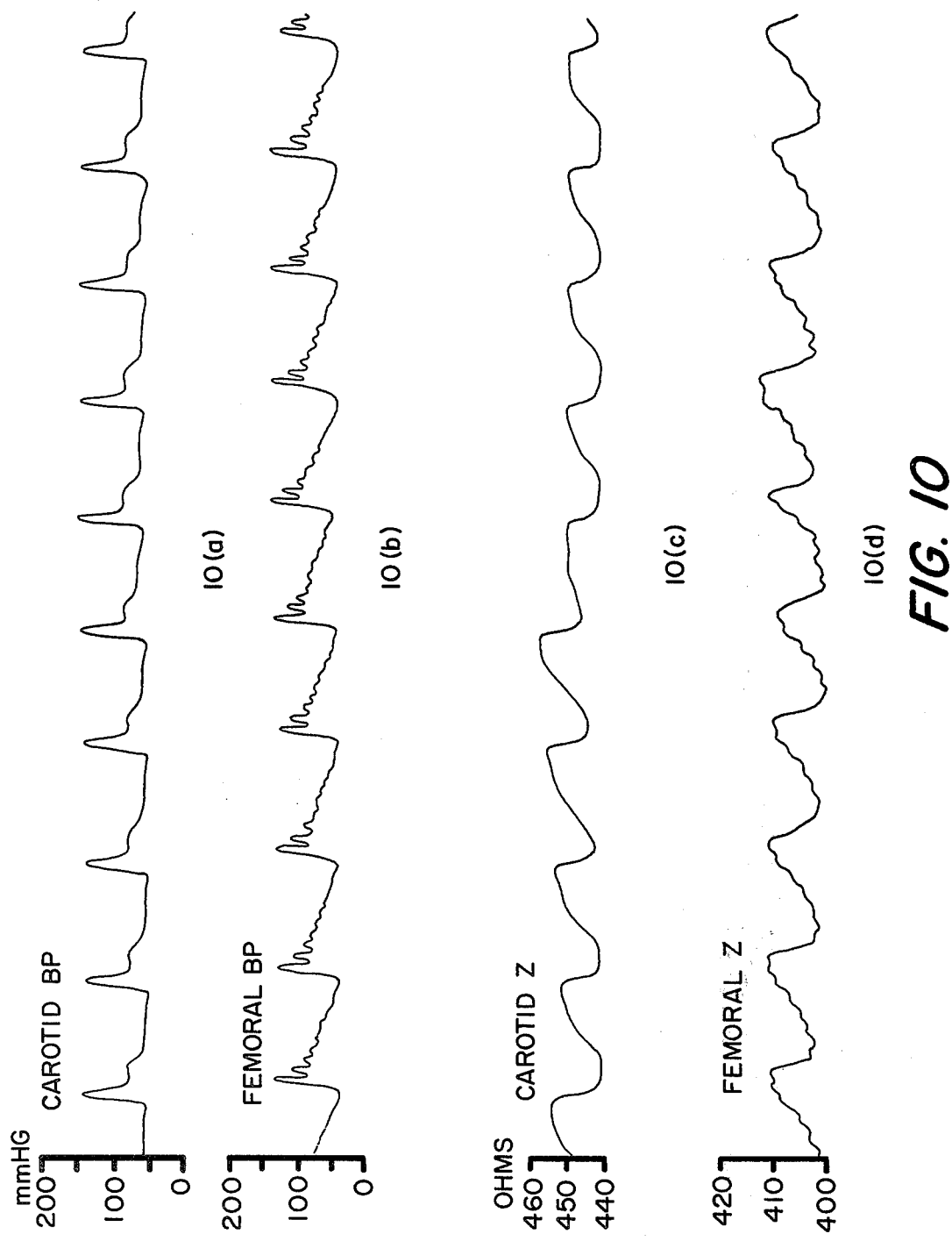

4,425,920

APPARATUS AND METHOD FOR MEASUREMENT AND CONTROL OF BLOOD PRESSURE

FIELD OF THE INVENTION

This invention relates to apparatus and method for measurement and control of blood pressure.

BACKGROUND OF THE INVENTION

One of the major medical problems today is that associated with lack of control of blood pressure in humans; indeed hypertension is a leading cause of disease and death in the United States. It has been reported that over fifteen percent of the United States population has hypertension at present, controlled by intermittent oral therapy or emergency intravenous medication.

For control of blood pressure, accurate and dependable measurement of blood pressure is necessary to both determine the presence of a problem and for monitoring the pressure to assure alleviation or control of such a problem. For best results, the measurement of blood pressure should be continuous. At present, however, blood pressure measurement is normally an intermittent process due to the constraints imposed by the pressure transducers available for utilization, which include a pressure cuff outside the body, which cuff cannot be maintained for long period of time on a human, or by an implanted transducer.

Implanted pressure transducers have been suggested that might enable continuous measurement of blood pressure. But such transducers have not been satisfactory in achieving pressure measurement that can be continuously maintained for relatively long periods. With respect to the implantable type of pressure transducer, it has been shown to be usable only for periods of up to ninety days. Even if such transducers could be developed to the point of providing long-life, problems would accrue due to the necessity for such transducers to be in direct contact with blood.

SUMMARY OF THE INVENTION

This invention provides apparatus and method for measuring and controlling blood pressure. The blood pressure is sensed by a measuring device capable of continuous measurement over an extended period with the indicated blood pressure measurement being utilized to cause drug release in a manner so as to alleviate any abnormal sensed indication of blood pressure.

It is therefore an object of this invention to provide an apparatus and method for measurement and control of blood pressure.

It is still another object of this invention to provide an apparatus and method for control of blood pressure by continuous sensing of such pressure and causing release of a drug to alleviate sensed abnormal indications with respect to such pressure.

It is another object of this invention to provide an apparatus and method for measurement of blood pressure that is capable of continuous measurement for an extended period of time.

It is still another object of this invention to provide an apparatus and method for measurement of blood pressure that monitors blood pressure without use of a pressure transducer.

With these and other objects in view, which will become apparent to one skilled in the art as the description proceeds, this invention resides in the novel combination, construction, arrangement of parts, and method substantially as hereinafter described, and more particularly defined by the appended claims, it being understood that such changes in the precise embodiment of the herein disclosed invention are meant to be included within the scope of the claims.

BRIEF DESCRIPTION OF THE DRAWINGS

The accompanying drawings illustrate a complete embodiment of the invention according to the best mode so far devised for the practical application of the principles thereof, and in which:

FIGS. 10(A) through (D) illustrate typical records of impedance pulses obtained with use of sleeve electrodes positioned along an artery.

DESCRIPTION OF THE INVENTION

Figure 1:
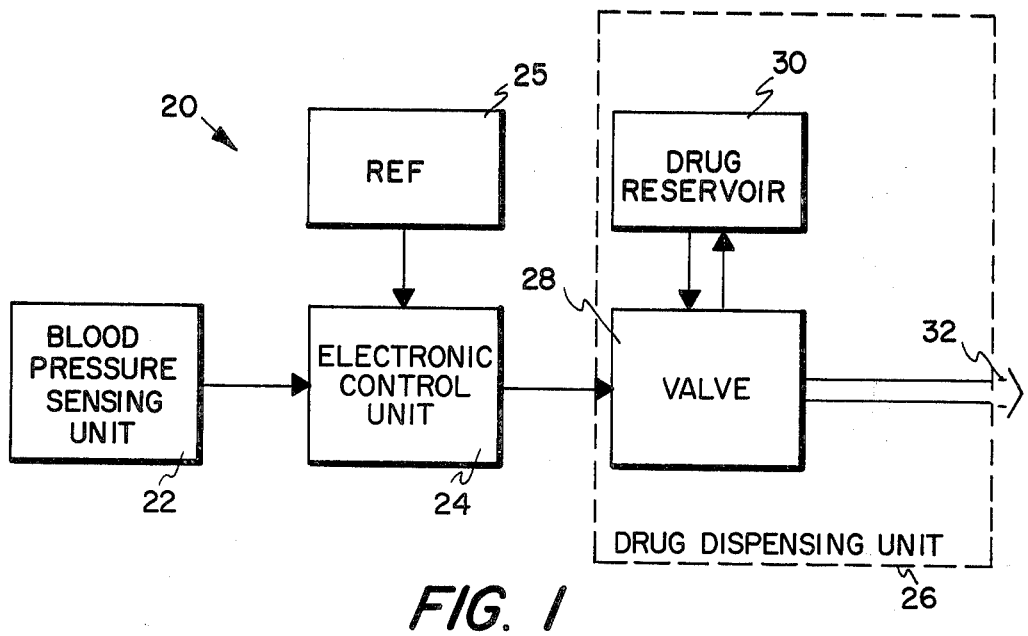
FIG. 1 is a block diagram of the measuring and controlling system of this invention.

Control apparatus 20 is preferably a fully automatic implantable blood pressure controlling system with long-life. It is to be realized, however, that apparatus 20 could be non-invasive (i.e., positioned outside the body) where needed or desired for particular applications. As shown in FIG. 1, apparatus 20 includes a sensing unit 22 to sense arterial blood pressure on a beat-by-beat basis, an electronic control unit 24 (having a reference unit 25 connected thereto), and a blood pressure effecting unit, such as a drug delivery unit 26. While not specifically shown, the blood pressure effecting unit might also, for example, include or consist of electrical nerve stimulation or biofeedback systems for control of blood pressure.

While blood pressure sensing unit 22 could be a conventional sensor of the implantable type, it is preferably a unit that does not include a pressure transducer but instead utilizes the relation between pulse transit time and diastolic blood pressure as the principle of transduction, as brought more fully hereinafter.

Electronic control unit 24 is preferably a microprocessor that relates monitored pulse transit times to an adjustable set-point, determined from clinical data. The set-point is made adjustable, as by non-invasive telemetric communication between the physician and the patient, to thereby set up conditions for comparison at control unit 24 with the pressure as measured by unit 22 and coupled to unit 24. If the measured pressure is outside the range of conditions, unit 24 opens a valve 28 in drug dispensing unit 26 to cause release of a suitable drug (such as sodium nitroprusside) from reservoir 30 through valve 28 to outlet 32 (a delivery catheter, for example) to cause injection of the drug into the body (i.e., a vein, for example) to thereby alleviate or correct the blood pressure and bring the same back within the acceptable region. While not shown, it is to be realized that control unit 24 could include sampling and averaging circuitry to accommodate transient rapid excursions of blood pressure without causing undue drug release.

Drug delivery, or dispensing, unit 26 is preferably a modified Infusaid pump presently produced by Metal Bellows Corporation, Sharon, Mass. Such pump is a hollow titanium disk separated into two chambers by a titanium bellows. Vapor pressure from a volatile flow of carbon liquid sealed in the outer chamber forces the drug from through a filter (preferably a 0.22 micron filter), a stainless steel capillary pressure drop mechanism, and a silicon rubber delivery catheter. The pump can be refilled by a percutaneous needle injection of the drug into the inner chamber through a self-sealing silicon rubber septum. The expansion of the bellows as the pump is filled condenses the flow of carbon vapor, thereby storing energy for the next infusion cycle. In this application, the rate of infusion is gated by valve 28 controlled by unit 24.

Figure 2:
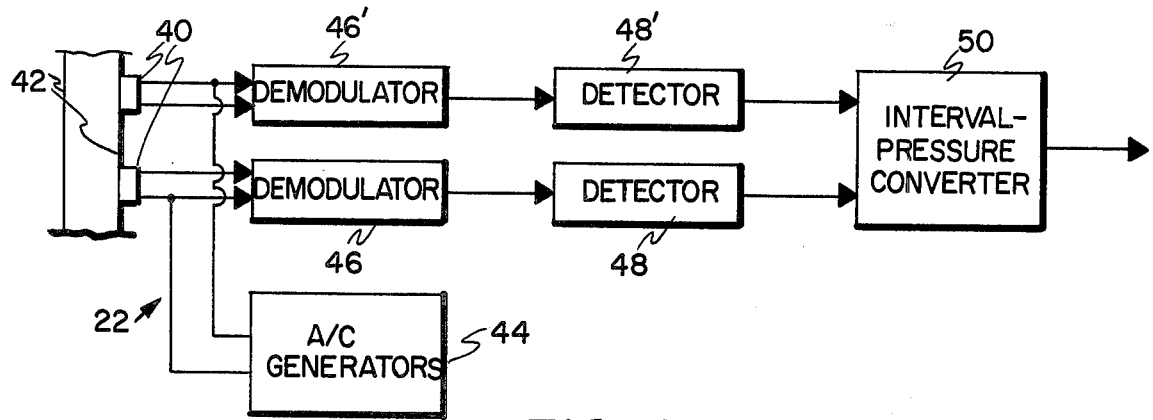
FIG. 2 is a block diagram of the measuring unit for providing an indication of blood pressure.

A blood pressure sensing unit 22 that does not require the use of a pressure transducer and which does not invade the blood stream since no direct blood contact is needed, is shown in the block diagram of FIG. 2. Instead, unit 22, as shown in FIG. 2, includes sets of electrodes 40 which are placed adjacent to the wall 42 of an artery of a body. Each set of electrodes 40 receives low level alternating current from generators 44, and the electrodes are connected with demodulators 46 and 46' which provide arterial pulses which are detected at detectors 48 and 48' to form pulses which are compared at interval-pressure converter circuit 50 and the resultant signal is coupled from unit 22 to electronic control unit 24 as the indication of measured blood pressure.

Unit 22 uses the well-known dependence of arterial pulse wave velocity upon blood pressure and the consequent decrease in pulse transit time within increasing blood pressure (i.e., they are inversely related). The arterial pulse is detected by continuously measuring the change in electrical impedance offered to a low level alternating current that appears between a set of electrodes placed alongside but outside of an artery. By using two electrodes sets positioned alongside the artery at different distances from the heart (with each set of electrodes preferably sensing impedance at different frequencies), pulse transit time, which is inversely related to blood pressure, is obtained without contact with the blood stream. Demodulation of the pulses results in arterial wave pulses, the time difference between which identifies blood pressure.

Since pulse transit time reflects blood pressure, it is in principle only necessary to detect the arrival of the pulse at two sites and extra-arterial pulse sensors can therefore be used. As long as pulse transit time is a stable, monotonic function of blood pressure in a given invididual, a satisfactory blood pressure controller can be utilized to sense in terms of transit time. Individual variations in the correlation between pulse transit time and blood pressure (for example, due to varying degrees of atherosclerosis) are unimportant, because a set-point for each implant is individualized in any case on the basis of clinical data.

A relationship between pulse wave velocity and blood vessel elasticity has heretofore been suggested for a quantitative indication of vascular disease. However, the diagnostic value of absolute pulse wave velocity is limited because it depends not only on the elasticity of the vessels, but also on their dimensions, both of which are non-linear functions of pressure. In addition, the relationship between pulse wave velocity and blood pressure has been demonstrated and the continuous mesurement of pulse wave velocity as a non-invasive indicator of changes in blood pressure in man has recently been advocated.

To prove that pulse transit time is an indicator of blood pressure, it is necessary to examine the physics underlying pulse propagation in a long tube. If a pressure pulse is introduced into a tube filled with fluid of a density $\rho$, and with a length l, diameter d, and thickness t, the velocity $V_p$ of the pulse wave is given by the Moens-Korteweg equation:

$$V_p = \sqrt{tE/\rho d}$$

where E is Young's modulus of elasticity (bulk stiffness) of the material that constitutes the tube (a larger value of E actually indicates a less elastic, i.e., stiffer, material).

Figure 3:
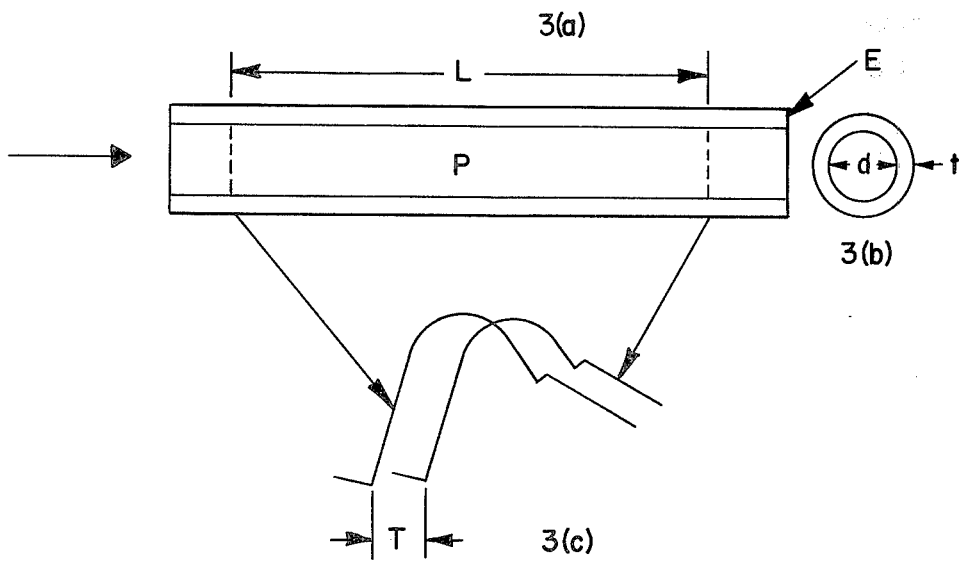
FIGS. 3 (A), (B), and (C) illustrate propagation of a pulse in a long thin-walled tube.

FIG. 3 illustrates the pulse transit time (T) as the pulse wave passes two points separated by L cm. Since the pulse is introduced and is propagated by the tube by virtue of its distension, the propagation velocity will be related to the pressure that exists when the pulse is introduced, i.e., diastolic pressure.

Pulse transit time T is merely the distance L traveled by the pulse, divided by the pulse wave velocity:

$$T = L/V_p$$

and the pulse wave velocity ($V_p$) is equal to $$\sqrt{\frac{tE}{\rho d}}$$

where E is the modulus of elasticity of the tube material and $\rho$ is the density of the fluid filling the tube.

Substituting to obtain pulse transit time in terms of the tube parameters:

$$T = L/\sqrt{\frac{tE}{\rho d}} = L\rho^{\frac{1}{2}}d^{\frac{1}{2}}t^{-\frac{1}{2}}E^{-\frac{1}{2}}$$

For pulse transit time to depend on blood pressure, one or more of the quantities in this expression must depend on blood pressure. Interestingly enough, the thickness t, diameter d, and modulus of elasticity E, are all pressure-dependent. With increasing pressure, the wall thickness diminishes, the diameter increases, and the modulus of elasticity increases very rapidly. Therefore, the type of relationship between pulse transit time and pressure depends on the manner in which these quantities vary together with pressure. Of the three, the increase in modulus of elasticity changes most with pressure. Thus, it is to be expected that the pulse transit time will decrease with increasing pressure. Since the pressure pulse is introduced at the level of diastolic pressure, pulse transit time will reflect diastolic pressure.

Figure 4:
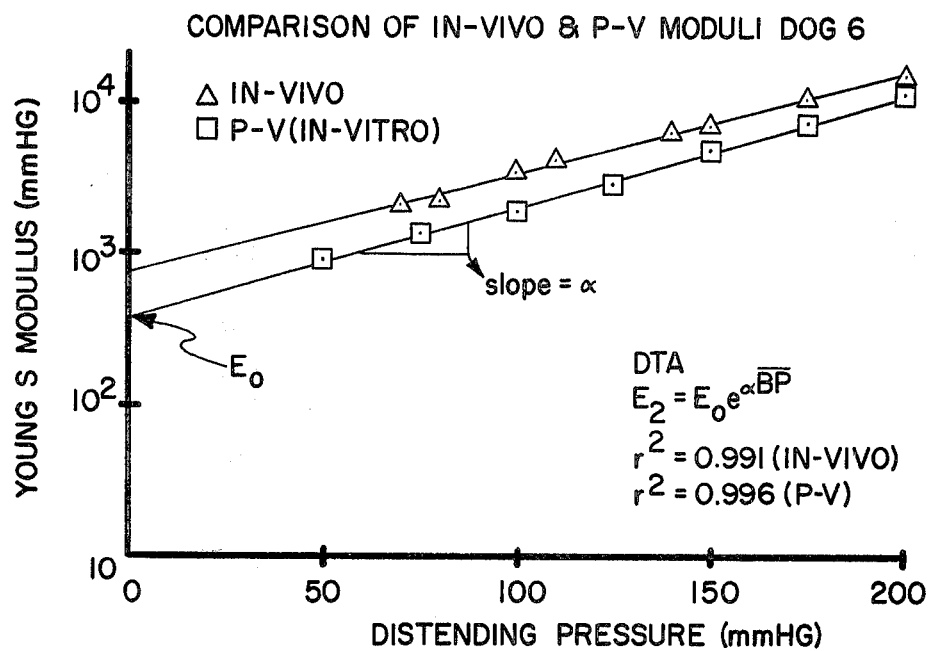
FIG. 4 is a plot illustrating the relationship between the modulus of elasticity and pressure for canine descending thoracic aorta.
Figure 5:
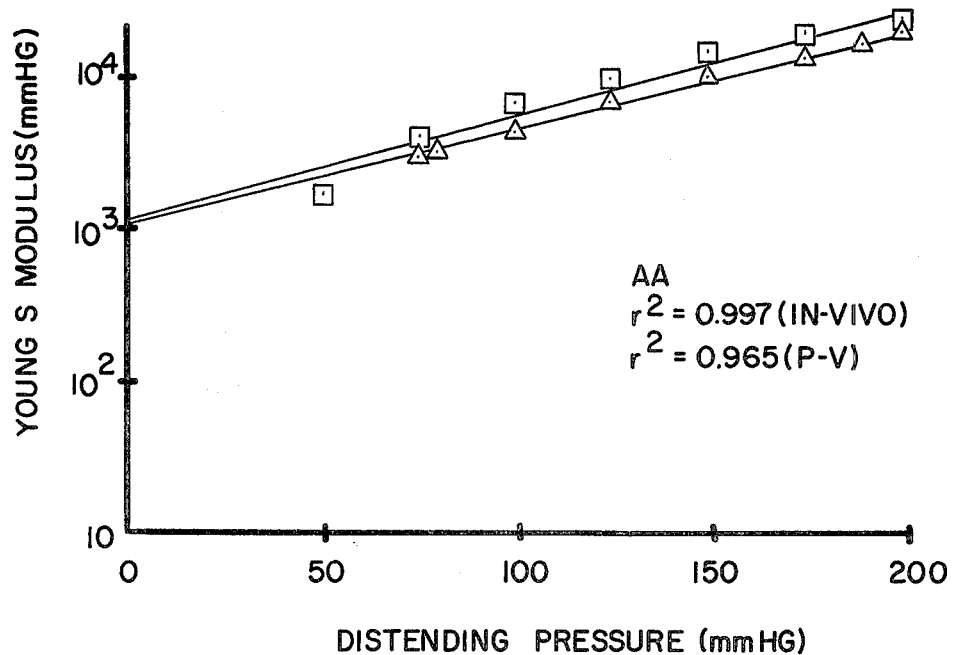
FIG. 5 is a plot illustrating the relationship between the modulus of elasticity and pressure for abdominal aorta.

It has been shown that the modulus of elasticity E, of the canine aorta increases exponentially with increasing pressure, according to the relation $E=E_o e^{aP}$, where $E_o$ is the zero pressure modulus and "a" is a constant dependent on the vessel. FIGS. 4 and 5 illustrate this relationship in semilogarithmic form for canine descending thoracic aorta (DTA) and for abdominal aorta (AA). For every 50 mmHg increase in blood pressure the elastic modulus doubles.

Figure 6:
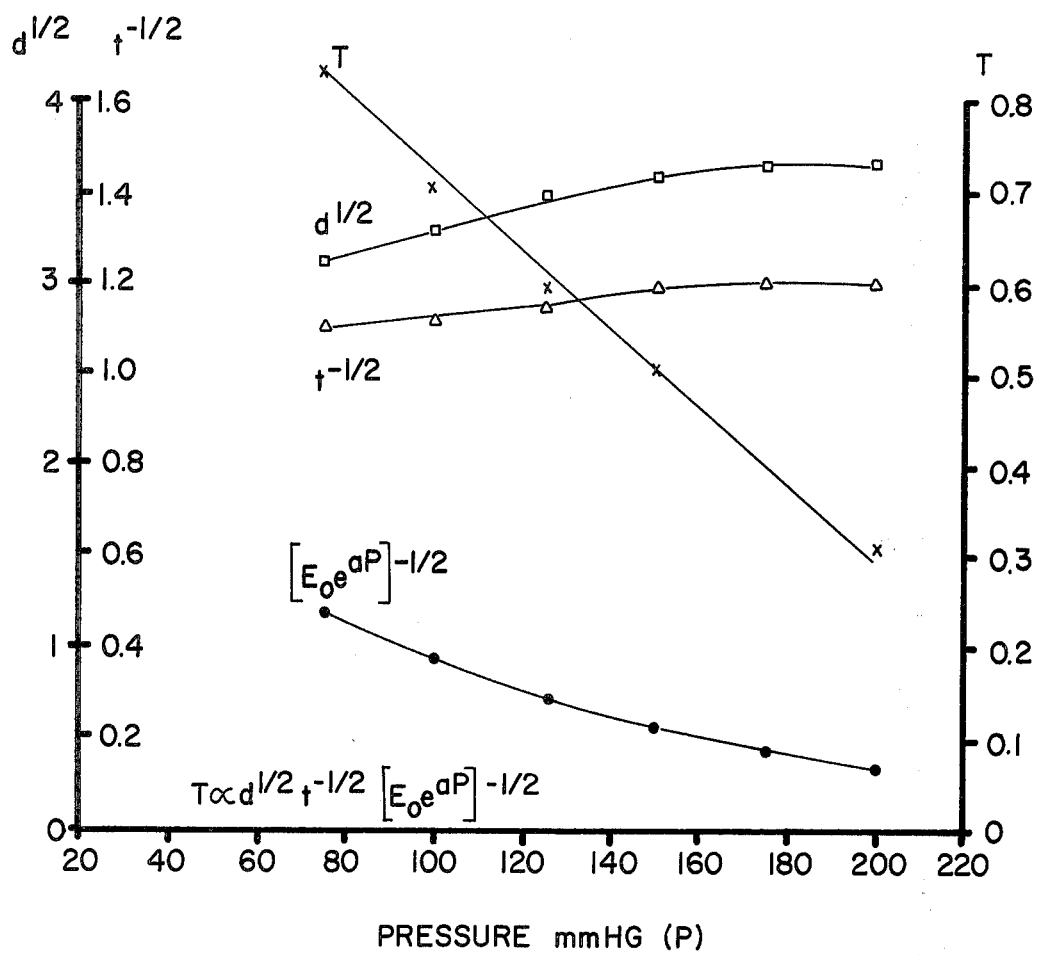
FIG. 6 is a plot of individual terms of the rearranged Moens-Korteweg equation of pressure for a canine aorta.

Using a triaxial ultrasonic catheter transducer within the canine aorta, the increase in diameter, decrease in wall thickness, and increase in stiffness with increasing diastolic pressure in vivo has also been minimal, with FIG. 6 being a plot of $$d^{\frac{1}{2}}, t^{-\frac{1}{2}}, E_o e^{aP-\frac{1}{2}} \text{ and } T$$

versus pressure. The pulse transit time, T, is proportional to the product of the three quantities. The percentage changes in the diameter and thickness terms are relatively small, and the net effect is a linear decrease T With increasing diastolic pressure.

Figure 7:
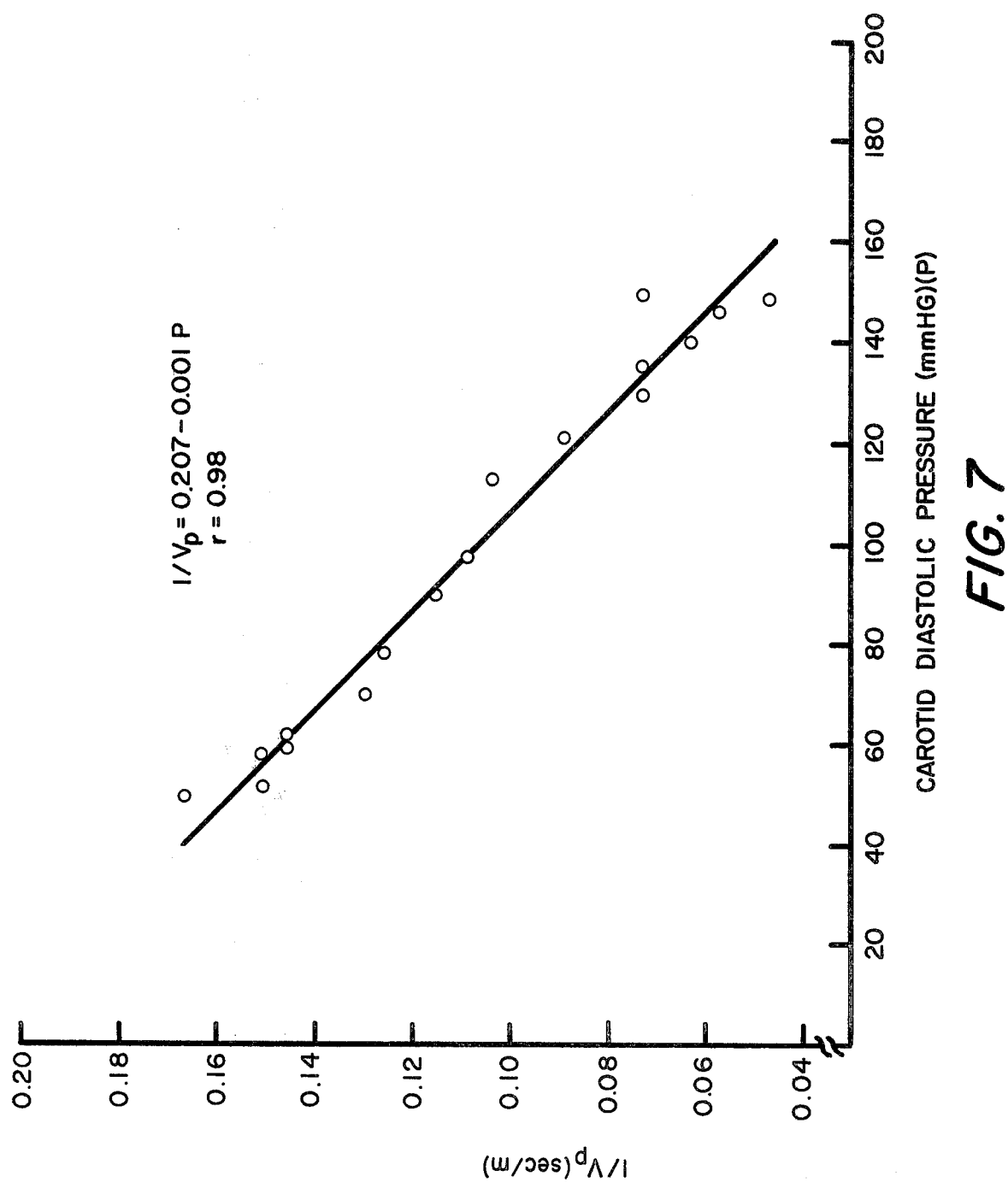
FIG. 7 is a plot illustrating the relationship between pulse transit time and diastolic blood pressure.

In order to verify that pulse transit time decreases with increasing diastolic pressure, transit time measurements were made in several dogs. Carotid and femoral artery pressures were recorded and the difference in arrival time between them was measured. The resultant value was a measure of the aortic pulse transit time. Diastolic pressure was reduced by vagal stimulation and increased by intravenous epinephrine. The relationship between carotid-to-femoral pulse transit time was measured over a pressure range extending from 40 to 250 mmHg. FIG. 7 shows the results of this study which indicate a linear decrease in pulse transit time (T) with an increase in blood pressure. This result also indicates that changes in pulse transit time can be used to indicate changes in blood pressure.

Because the internal environment is so hostile to non-hermetically sealed implants, no long-life pressure transducers now exist. However, experience with pacemakers has proven that implanted electrodes have an extremely long life and would therefore be excellent components in an arterial pulse sensing system.

Figure 8:
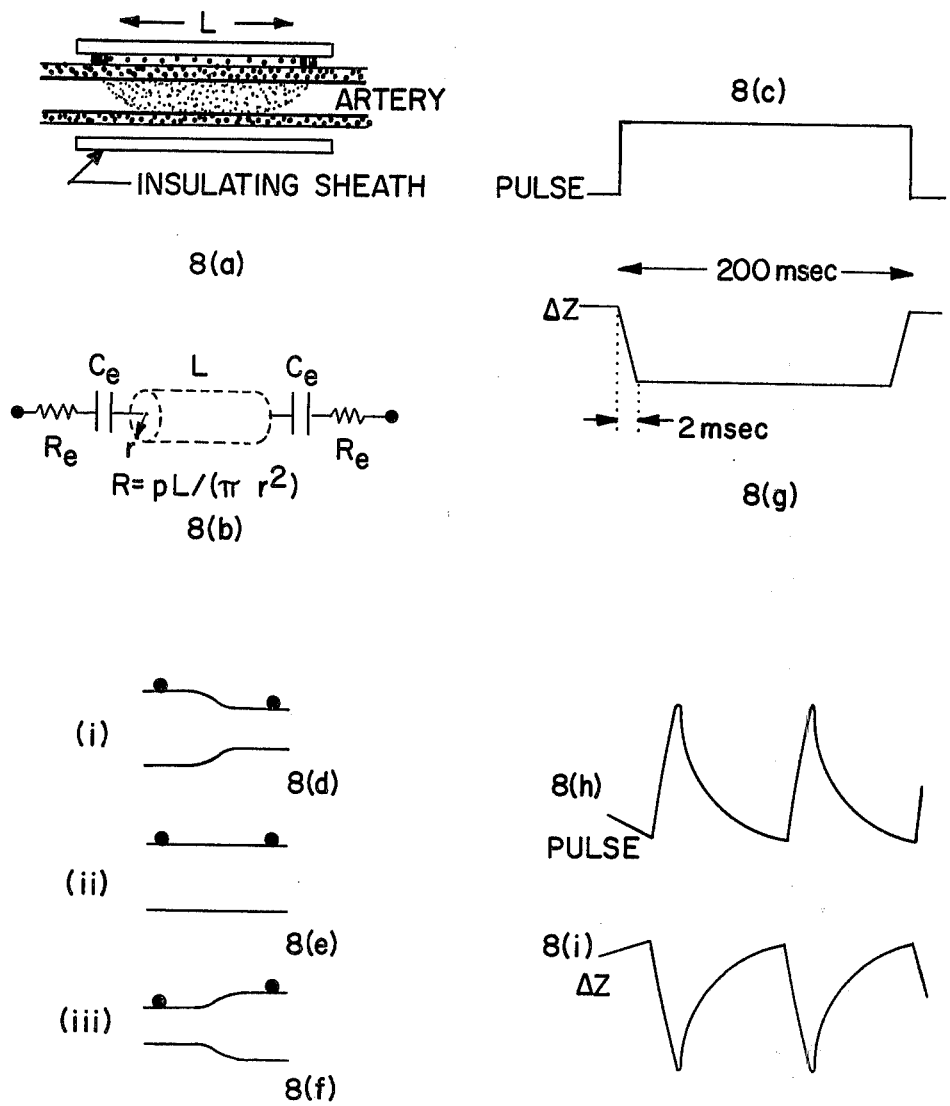
FIGS. 8(A) through (I) are illustrations relating to the principles of pulse detection with extravascular electrodes.

FIG. 8 illustrates the principles of pulse detection with extravascular electrodes. Suppose two point electrodes are applied to the adventitia of an artery a longitudinal distance, L, apart and surrounded with an insulating sleeve. Current passing between the electrodes is constrained to flow through the artery roughly as indicated by the dotted lines in FIG. 8 (A). With this electrode arrangement, the approximate changes in inter-electrode impedance with the arterial pulse can be predicted from the equivalent circuit shown in FIG. 8 (B). Each electrode impedance can be modeled as series RC elements which do not change with the pulse. The reactances of the electrode capacitance are negligible at the frequency of the impedance-sensing currents. For completeness, we also include the electrode resistances. Then, the intervening column of blood and arterial wall may be modeled approximately as a conductive cylinder, the impedance of which is entirely resistive and given by the expression, $$\rho L/(\pi r^2)$$

where $\rho$ is the net resistivity of blood and wall tissue, and L and r represent the effective length and radius of the conductive cylinder. The entire impedance, Z, between the electrodes is given by the sum of the electrode impedances, $Z_e$, and the impedance of the blood-issue cylinder $$Z = Z_e + \rho L/(\pi r^2) + Z_e$$

With each pulse, the effective radius of the conductive cylinder increases, while the other terms contributing to Z remain essentially constant. Hence, with this electrode arrangement one would predict a decrease of impedance with each pulse. (Note, incidentally, that such a decrease in impedance would not necessarily occur with transversely placed electrodes, since the pulse would increase the inter-electrode length as well as the inter-electrode area.)

The shape of the arterial impedance pulse detected with such electrodes as a function of time can be appreciaed with reference to FIG. 8(C) which illustrates, for iitial consideration, the passage of a rectangular pulse beneath the two electrodes. Three stages of passage are identified in FIGS. 8(D), 8(E) and 8(F). In the first (shown in FIG. 8(D)), the pulse appears under the proximal electrode, in the second (shown in FIG. 8(E)), the pulse is present under both electrodes, and in the third (shown in FIG. 8(F)), the pulse remains only under the distal electrode. The impedance change, $\Delta Z$, caused by the rectangular pressure pulse can be calculated by convolving the pressure pulse with a rectangular pulse which has a duration equal to the time required for the pressure pulse to traverse the distance separating the electrodes, this is, from theoretical considerations, $$\Delta Z(t) = \int P(t-u) R(u) du,$$

where:
$\Delta Z$ = impedance signal recorded from electrodes,
P = arterial pressure pulse, and
R = rectangular pulse (time window) corresponding to electrode separation.

The result, illustrated for a hypothetical rectangular arterial pulse in FIG. 8(G), is a blunting of rapid changes in the pulse wave which is dependent upon electrode separation.

Too large a separation between the electrodes could alter the detected waveform. However, since the arterial pulse wave velocity is on the order of 5 mm/msec, the time any point in the pulse wave spends between the two electrodes is roughly 2 msec for every centimeter of electrode separation, L. This period may be compared with the duration of the entire arterial pulse which is on the order of several hundred milliseconds duration, one can expect the impedance signal to correspond to an inverted image of the pulse wave (as shown in FIGS. 8(B) and 8(C)), which reflects the increase in arterial diameter as the pulse passes the sensing electrodes.

Figure 9:
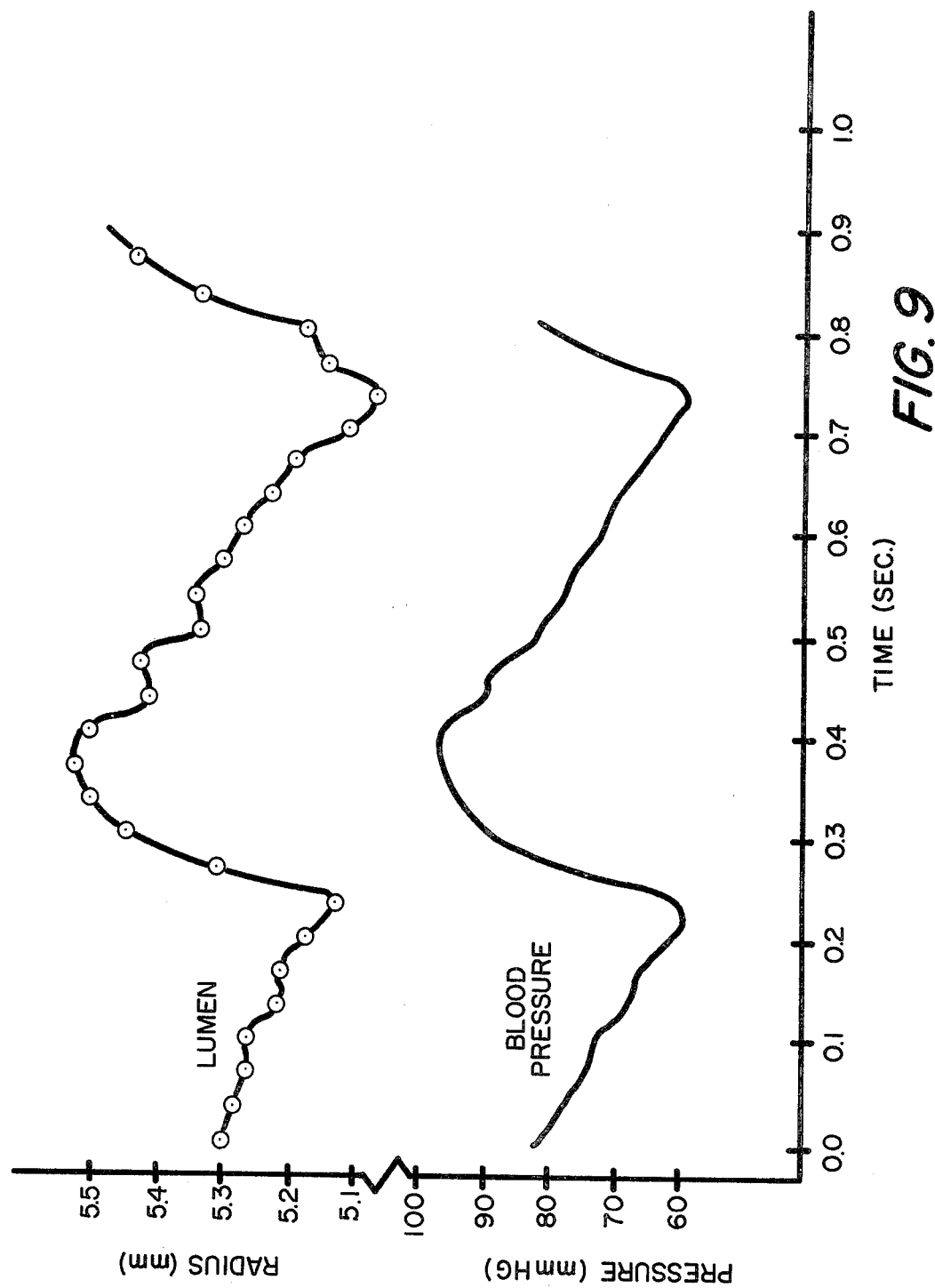
FIG. 9 is a comparison of lumen and blood pressure waveforms.

Having predicted the shape of the impedance pulse signal, one may go on to estimate its magnitude. It has been shown that for canine thoracic and abdominal aorta in situ the ultrasonically measured internal diameter changes approximately seven percent (7%) with the pulse wave in pattern similar in the time domain to the arterial pressure trace (See FIG. 9).

Using the model and equivalent circuit above described, one can calculate the magnitude of the impedance change expected from the change in radius of the conductive cylinder between the electrodes from the expression $$\Delta Z = \rho \frac{L}{\pi r^2} - \rho \frac{L}{\pi (r + \Delta r)^2} = \rho \frac{L}{\pi r^2} \left( 1 - \frac{1}{(1 + \Delta r/r)^2} \right)$$

An advantage of increased electrode separation, L, is increased signal amplitude; a disadvantage, perhaps, is ambiguity in measuring site location as well as blunting of the leading edge of the detected signal. For example, considering a canine carotid or femoral artery of radius approximately 3 mm, a pulse-induced change in vessel radius of seven percent (7%), a blood resistivity of 150 ohm-sm, and an effective cylinder length of 0.5 cm between sensing electrodes 1 cm apart; the expected impedance signal should be on the order of 30 ohms.

Using a bipolar sleeve electrode wrapped about an artery, measurements were made of the impedance pulse between longitudinal electrodes placed 1 cm apart alongside the carotid artery and the femoral artery of an anesthetized dog. FIGS. 10(A) and 10(B) illustrate typical records obtained with this electrode placement, and using a 25 KHz current, as expected, the impedance pulse is an inverted image of the arterial pressure pulse. The amplitude of the impedance signal is about 10 ohms, which is on the same order as the 30 ohms predicted from theory. The rapid downstroke in the impedance waveform correlates with the pulse arrival time. Note that the transit times of the pressure pulses from the carotid to femoral arteries are clearly identified in both the pressure and impedance channels. (Some of the bandwidth limitation, evidenced by a slower rise time of the impedance pulses compared to the pressure pulses in FIG. 10 is due to the particular recorder used in this study and not to electrode suparation.) These findings show that differences in impedance pulse arrival time, detected with implanted extra-vascular electrodes, can be used to measure pulse arrival time.

In summary, the foregoing theory and testing indicate that the impedance pulse signal from a longitudinally placed electrode will have:

(1) a rise time of a few milliseconds for electrode placements a few centimeters apart;

(2) a waveform which is an inverted image of the pulse; and (3) an amplitude determined by the factors in the expression $$\Delta Z = \rho \frac{L}{\pi r^2} \left[ 1 - \frac{1}{(1 + \Delta r/r)^2} \right]$$

Since it has been demonstrated in vivo the ratio, $\Delta r/r$, is a function of the ratio of pulse pressure to mean distending pressure, and blood resistivity, $\rho$, is an exponential function of hematocrit, it can be reasonably predicted that the amplitude of the impedance signal will be

| increased for | decreased for |
|---|---|
| increased hematocrit | hemodilution |
| increased inter- | more closely |
| electrode length | spaced electrodes |
| smaller vessels | larger vessels |
| decreased mean distending pressure | increased mean distending pressure |
| increased pulse pressure | decreased pulse pressure |

As can be appreciated from the foregoing, this invention can be utilized as an implantable therapeutic device and/or for continuous patient monitoring in a critical care area. When used as an automatic control device for drug delivery to control, for example, high blood pressure, the drug will be released only as necessary to cause the blood pressure to decrease within the desired range and then to be maintained within that range. In addition, since the sensing unit does not include a pressure transducer, there is no need to invade or impede the blood stream to measure pressure.

What is claimed is:

1. An apparatus for measuring blood pressure, said apparatus comprising:

a pair of electrode sets for positioning adjacent to and outside an artery;

alternating current generator means for providing alternating current to each of said electrode sets;

first and second demodulator means each of which is connected with a different one of said electrode sets for forming pulses in response to receipt of signals from said electrode sets due to the impedance offered to said alternating current between the electrodes of said electrode sets to thereby determine the pulse transit time of blood flowing through said artery;

first and second detector means each of which is connected with a different one of said first and second demodulator means to indicate the time of arrival of pulses from said demodulator means and form therefrom arterial pulse waves; and time interval measuring means connected with said first and second detector means for receiving said arterial pulse waves therefrom and responsive thereto providing an electrical signal output that is indicative of blood pressure sensed in said artery.

2. A method for measuring blood pressure in a body, said method comprising:

positioning sets of electrodes along and outside an artery having blood flowing therethrough;

applying an alternating current to said electrodes;

determining the pulse transit times between said electrodes of each of said sets of electrodes by separately demodulating the sensed impedance offered to said alternating current between the electrodes of each said set of electrodes and producing therefrom representations of arterial pulses;

separately detecting the arterial pulses to form arterial pulse waves; and comparing the arterial pulse waves to provide therefrom a signal indicative of the pressure of said blood flowing through said artery.

3. The method of claim 2 wherein said impedance between each said set of electrodes is determined at different frequencies.

* * * * *